United States Patent
Star et al.

(10) Patent No.: US 9,482,638 B2
(45) Date of Patent: Nov. 1, 2016

(54) GRAPHENE COMPOSITION, METHOD OF FORMING A GRAPHENE COMPOSITION AND SENSOR SYSTEM COMPRISING A GRAPHENE COMPOSITION

(71) Applicant: University of Pittsburgh—Of the Commonwealth System of Higher Education, Pittsburgh, PA (US)

(72) Inventors: Alexander Star, Pittsburgh, PA (US); Narasimha Harindra Vedala, Pittsburgh, PA (US); Gregg Peter Kotchey, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/554,912

(22) Filed: Nov. 26, 2014

(65) Prior Publication Data
US 2015/0086977 A1 Mar. 26, 2015

Related U.S. Application Data

(63) Continuation of application No. 13/370,076, filed on Feb. 9, 2012, now Pat. No. 8,920,764.

(60) Provisional application No. 61/441,925, filed on Feb. 11, 2011.

(51) Int. Cl.
| | | |
|---|---|---|
| *G01N 27/414* | (2006.01) | |
| *G01N 33/569* | (2006.01) | |
| *G01N 33/543* | (2006.01) | |
| *G01N 27/12* | (2006.01) | |
| *B82Y 30/00* | (2011.01) | |
| *B82Y 40/00* | (2011.01) | |
| *C01B 31/04* | (2006.01) | |
| *C12P 3/00* | (2006.01) | |

(52) U.S. Cl.
CPC ............ *G01N 27/4146* (2013.01); *B82Y 30/00* (2013.01); *B82Y 40/00* (2013.01); *C01B 31/0476* (2013.01); *C01B 31/0484* (2013.01); *C12P 3/00* (2013.01); *G01N 27/127* (2013.01); *G01N 27/4145* (2013.01); *G01N 33/5438* (2013.01); *G01N 33/56916* (2013.01); *G01N 2333/245* (2013.01); *Y10S 977/734* (2013.01); *Y10S 977/898* (2013.01)

(58) Field of Classification Search
CPC ...................................................... C01B 31/04
USPC ................................................. 423/448, 460
See application file for complete search history.

(56) References Cited

U.S. PATENT DOCUMENTS

2009/0146111 A1\* 6/2009 Shin et al. ..................... 252/510
2010/0105834 A1\* 4/2010 Tour et al. ...................... 525/50

OTHER PUBLICATIONS

Jiang, et al., Porous Graphene as the Ultimate Membrane for Gas Separation, Nano Letters 2009; 9(12): 4019-4024.\*
Garaj, et al., Graphene as a subnanometre trans-electrode membrane, Nature 2010; 467: 190-194.\*
The ARRL Handbook for Radio Communications, p. 3.12 (ARRL 2014).\*

\* cited by examiner

*Primary Examiner* — Daniel C McCracken
(74) *Attorney, Agent, or Firm* — Bartony & Associates, LLC

(57) ABSTRACT

A device including a composition formed by oxidation of graphene oxide to form holey graphene oxide having defects therein and reduction of the holey graphene oxide. A composition includes graphene oxide sheets including holes therein formed by oxidation to form a network of interconnected graphene oxide nanoribbons.

20 Claims, 6 Drawing Sheets

GRAPHENE COMPOSITION, METHOD OF FORMING A GRAPHENE COMPOSITION AND SENSOR SYSTEM COMPRISING A GRAPHENE COMPOSITION

CROSS-REFERENCE TO RELATED APPLICATIONS

This application is a continuation of U.S. patent application Ser. No. 13/370,076, filed Feb. 9, 2012, which claims benefit of U.S. Provisional Patent Application Ser. No. 61/441,925, filed Feb. 11, 2011, the disclosures of which are incorporated herein by reference.

STATEMENT OF GOVERNMENT INTEREST

This invention was made with government support under Grant No. RO1ES019304 awarded by the National Institutes of Health. The government has certain rights in this invention.

BACKGROUND OF THE INVENTION

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Graphene has attracted significant attention as a result of its novel electronic properties coupled with its mechanical strength. Both such properties may make graphene an important material in future generations of electronics, batteries, sensors, composites etc. One of the current methods of synthesizing graphene entails exfoliating graphite through oxidation to yield graphite oxide. That material is sonicated to produce graphene oxide. Graphene oxide is subsequently reduced either chemically or thermally to produce reduced graphene oxide (RGO).

While the graphene precursor, graphite oxide, has been studied for about 170 years, there is now emerging interest in graphene oxide and RGO. For example, graphene oxide has been proposed for drug delivery and cellular imaging applications. Further, graphene oxide paper formed from interlocking sheets of graphene oxide demonstrated superior strength and stiffness compared to many other papers. Finally, graphene oxide has been suggested as a simple alternative to poly(3,4-ethylenedioxythiophene)-poly(styrenesulfonate) (PEDOT:PSS), a hole transporting layer and electron blocking layer in organic photovoltaics (OPVs). RGO, on the other hand, has been employed for both chemical and biological sensing applications.

Graphene and graphene derivatives such as graphene oxide have been modified for applications through treatment with strong oxidizing and reducing agents, oxidative etching at temperatures greater than 400° C., etching using lithography, and sonochemical approaches.

SUMMARY OF THE INVENTION

In one aspect, a method of forming or synthesizing a composition includes oxidation of graphene oxide and reduction of the graphene oxide after oxidation thereof. Oxidation of graphene oxide forms defects therein (holes, pores etc.). The resultant "holey" graphene oxide is then reduced. The reduction of the holey oxidized graphene oxide may, for example, be carried out thermally (via heating) or chemically (using a reducing agent which may, for example, include hydrazine hydrate). The oxidation may, for example, be effected using various oxidizing reactants. In a number of embodiments, oxidation of graphene oxide includes enzymatic oxidation of graphene oxide. The enzymatic oxidation may occur in the presence of a peroxidase and a substrate for the peroxidase. For example, the peroxidase may be horseradish peroxidase (HRP), myeloperoxidase (MPO), cytochrome c peroxidase, cytochrome P450, eosinophil peroxidase, glutathione peroxidase, lactoperoxidase, thyroid peroxidase, deiodinase, lignin peroxidase, or manganese peroxidase. The substrate may, for example, include a peroxide such as hydrogen peroxide or an organic hydroperoxide.

Enzymatic oxidation may, for example, be effected using relatively mild reaction conditions and without significantly adverse effects to the environment. The oxidation of graphene oxide may, for example, be carried out in a temperature range of approximately 20° C. to 90° C. or approximately 20° C. to 40° C. Moreover, enzymatic oxidation may be well controlled over a variety of conditions. Oxidation, may, for example, be controlled in a manner to provide holes or pores in the graphene oxide. For example, holes may be formed in the basal plane of graphene oxide during oxidation to form holey graphene oxide. Reaction conditions including, for example, reaction time, frequency of addition of substrate, concentration of substrate added may be varied as described herein using techniques known to those skilled in the art to control the properties of the holey graphene oxide (for example, hole diameter and neck width).

In another aspect, a composition is formed by a process including oxidation of graphene oxide to form holey graphene oxide having defects therein and reduction of the holey graphene oxide. As described above, reduction of the oxidized graphene oxide may, for example, be carried out thermally (via heating) or chemically (using a reducing agent which may, for example, include hydrazine hydrate). The oxidation may, for example, be effected using various oxidizing reactants. As further described above, in a number of embodiments, the oxidation of graphene oxide includes enzymatic oxidation of graphene oxide in the presence of a peroxidase and a substrate for the peroxidase.

In another aspect, a composition includes a graphene oxide member comprising defects (hole, pores, etc.) therein formed by oxidation. The graphene oxide member may be reduced (for example, via thermal reduction of via chemical reduction). The oxidation may, for example, be enzymatic oxidation.

In a further aspect, a device includes a component including a composition formed by oxidation of graphene oxide and reduction of the graphene oxide after oxidation thereof. As described above, oxidation of the graphene oxide may be enzymatic oxidation in the presence of a peroxidase and a substrate for the peroxidase.

The component may, for example, include a field-effect transistor in which a conductive path is formed using the composition. In a number of embodiments, the device is a sensor for sensing an analyte in which a conductive path is formed using the composition. In a number of embodiments, a material interactive with the analyte is immobilized upon the reduced graphene oxide members. In a number of embodiments, a plurality of reduced graphene oxide members are immobilized on a substrate (for example, via dielectrophoresis). The conductive path may, for example, be positioned between two electrodes. The conductive path and electrodes may, for example, form a portion of a field-effect transistor system.

In still a further aspect, a method of sensing an analyte includes measuring a change in an electrical (either a.c or d.c) or electrochemical characteristic of a conductive path including a plurality of reduced graphene oxide members having defects (hole, pores, etc.) formed therein. In a number of embodiments, a material interactive with the analyte is immobilized upon the reduced graphene oxide members.

HRP catalyzed oxidation of graphene oxide results in the formation of defects or holes in the basal plane of this nanomaterial. The holey graphene nanostructures produced by enzymatic oxidation of graphene oxide demonstrate p-type semiconducting behavior upon reduction. In a number of embodiments of holey reduced graphene oxide devices, at least one species which interacts with an analyte is placed in operative connection with or immobilized upon holey reduced graphene oxide to form sensors that are sensitive to a number the analytes. Moreover, with proposals for graphene oxide to be implemented in applications with an environmental impact, enzymatic oxidation may also be an attractive method for the bioremediation of graphene oxide.

The present invention, along with the attributes and attendant advantages thereof, will best be appreciated and understood in view of the following detailed description taken in conjunction with the accompanying drawings.

DETAILED DESCRIPTION OF THE INVENTION

Figure 1A:
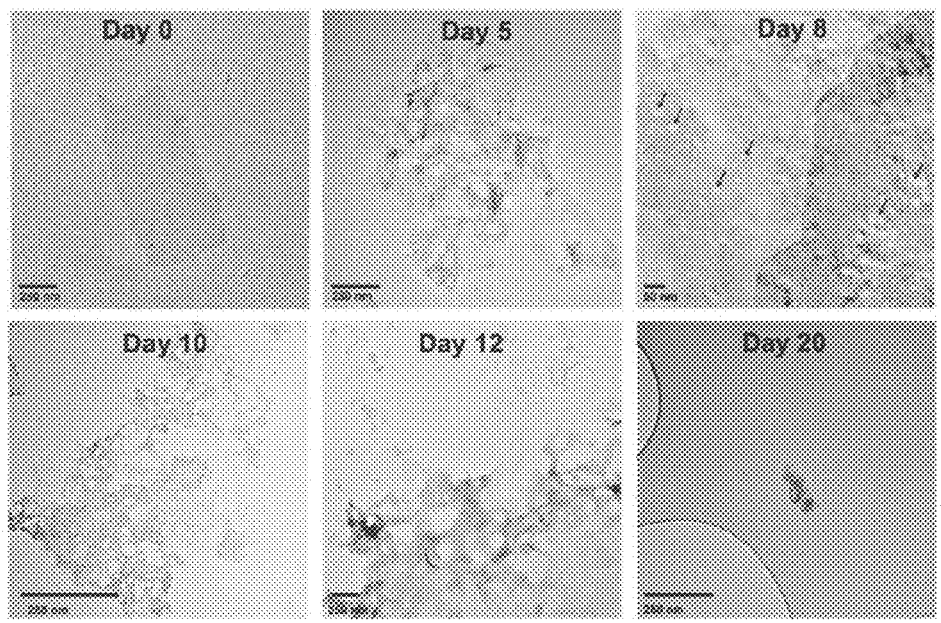
FIG. 1A illustrates transmission electron microscopy (TEM) photographs monitoring the progression of a peroxidase (horseradish peroxidase or HRP) catalyzed oxidation of graphene oxide over a 20 day period with daily additions of 40 μM $H_2O_2$ (final concentration).

As used herein and in the appended claims, the singular forms "a," "an", and "the" include plural references unless the content clearly dictates otherwise. Thus, for example, reference to "a peroxidase" includes a plurality of such peroxidases and equivalents thereof known to those skilled in the art, and so forth, and reference to "the peroxidase" is a reference to one or more such peroxidases and equivalents thereof known to those skilled in the art, and so forth.

The studies hereof demonstrate mild enzymatic oxidation of graphene oxide resulting in the formation of holey graphene oxide nanostructures. The stability of reduced graphene oxide or RGO towards oxidation by peroxidases was also demonstrated. Further, it was shown that enzymatic treatment of graphitic materials (for example, nanomaterials) hereof resulted in alterations of their electronic properties. It was found that holey reduced graphene oxide (hRGO), the reduced form of holey graphene oxide, demonstrated p-type semiconducting behavior, which makes this material desirable for a number of applications, including, for example, field-effect transistors (FETs).

As described above, in a number of compositions hereof, graphene oxide is oxidized (for example, via enzymatic oxidation). Enzymatic oxidation introduces defects in the basal plane of graphene oxide to enable alteration of the electronic transport properties of the reduced form thereof (for example, via a change/increase in an edge to plane ratio). Enzymatic oxidation can lead to the formation of holes in graphene oxide. Such holes can, for example, have an average diameter in the range of approximately 1 to 100 nm. A peroxidase enzyme can, for example, be used to effect enzymatic oxidation. In a number of representative studies hereof, horseradish peroxidase was used. After enzymatic oxidation of graphene oxide, reduction of the material may, for example, be effected via a chemical technique or via heating. In a number of studies, reduction with reducing agent such as hydrazine hydrate was carried out after enzymatic oxidation to provide holey reduced graphene oxide or hRGO.

Peroxidases suitable for use in oxidizing graphene oxide include, for example, horseradish peroxidase (HRP), myeloperoxidase (MPO), cytochrome c peroxidase, cytochrome P450, eosinophil peroxidase, glutathione peroxidase, lactoperoxidase, thyroid peroxidase, deiodinase, lignin peroxidase, and manganese peroxidase. Suitable buffers include, for example, formates, citrates, succinates, acetates, propionates, malates, pyridines, piperazines, cacodylates, succinates, 2-(N-morpholino)ethanesulfonic acid (MES), maleates, histidine, bis-tris, phosphates, ethanolamine,s ADA (N-(2-acetamido)iminodiacetic acid), carbonate, N-(2-Acetamido)-2-aminoethanesulfonic acid (ACES), piperazine-N,N'-bis(2-ethanesulfonic acid (PIPES), 3-(N-Morpholino)-2-hydroxypropanesulfonic acid (MOPSO), imidazoles, 1,3-bis(tris(hydroxymethyl)methylamino)propane (BIS-TRIS propane), Phosphate buffered saline (PBS), N,N-Bis(2-hydroxyethyl)-2-aminoethanesulfonic adic (BES), 3-(N-morpholino)propanesulfonic acid (MOPS), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 4-(N-morpholino)butanesulfonic acid (MOBS), 3-[N,N-bis(2-Hydroxyethyl)amino]-2-hydroxypropanesulfonic acid (DIPSO), 3-[[1,3-dihydroxy-2-(hydroxymethyl)propan-2-yl]amino]-2-hydroxypropane-1-sulfonic acid (TAPSO), triethanolamine (TEA), pyrophosphate, 4-(2-Hydroxyethyl)-piperazine-1-(2-hydroxy)-propanesulfonic acid (HEPPSO), 2-hydroxy-3-[4-(2-hydroxy-3-sulfopropyl)piperazin-1-yl] propane-1-sulfonic acid (POPSO), tricine, hydrazine, glycylglycine, 2-Amino-2-hydroxymethyl-propane-1,3-diol (Trizma or Tris), 3-[4-(2-Hydroxyethyl)-1-piperazinyl]propanesulfonic acid (EPPS or HEPPS), Diethylolglycine; DHEG; N,N-Di-(Hydroxyethyl)glycine (BICINE), N-(2-Hydroxyethyl)piperazine-N'(4-butanesulfonic acid (HEPBS), 3-[[1,3-dihydroxy-2-(hydroxymethyl)propan-2-yl]amino]propane-1-sulfonic acid (TAPS), 2-amino-2-methyl-1,3-propanediol (AMPD), N-tris(hydroxymethyl)-4-aminobutanesulfonic acid (TABS), N-(1,1-Dimethyl-2-hydroxyethyl)-3-amino-2-hydroxypropanesulfonic acid (AMPSO), taurine (AES), borate, 2-(Cyclohexylamino)ethanesulfonic acid (CHES), 2-amino-2-methyl-1-propanol (AMP), glycine, ammonium hydroxide, N-cyclohexyl-2-hydroxyl-3-aminopropanesulfonic acid (CAPSO), carbonate, methylamine, N-cyclohexyl-3-aminopropanesulfonic acid (CAPS).

The conditions under which enzymatic oxidation of graphene oxide can occur vary over a wide range. For example, in a number of embodiments, temperature can range over approximately 20° C. to 90° C. or even 20° C. to 40° C. In a number of representative embodiments, the temperature was approximately 25° C. (room temperature) or approximately 37° C. pH may, for example, be in the range of 3.0 to 10.0. In a number of representative studies, pH was in the range of 7.0 to 7.4. Final substrate ($H_2O_2$ in the representative studies) concentration may, for example, be in the range of approximately 0 to 100 mM. Final enzyme concentration may, for example, be in the range of approximately 0 to 10 000 U/mL. In a number of embodiments, NaCl is present in the range of concentrations of approximately 0 to 1.0 M or approximately 0 and 140 mM and KCl is present in the range of concentrations of approximately 0-100 mM or approximately 0 and 2.7 mM. Hydrogen peroxide or other substrate (for example, an organic hydroperoxide) can be added over period of minutes or days.

Various electrical (a.c or d.c) and electrochemical devices may, for example, be formed using hRGO material. Such devices may, for example, be easily integrated with available and future developed complementary metal-oxide-semiconductor (or CMOS) technologies, which are, for example, used in constructing integrated circuits. The devices hereof can, for example, be formed as field effect transistors (or FETs).

For example, sensors adapted to sense an analyte may include a conductive path formed from hRGO members. In a number a studies hereof, materials that interact with an analyte are immobilized on the hRGO materials. Such interactive materials may, for example, be deposited upon the hRGO materials or covalently bound thereto. Interaction of the analyte with such materials causes electrical changes which can be detected (for example, changes in conductance). Metals may, for example, be deposited upon or decorated upon holey reduced graphene oxide or hRGO. The sensor may, for example, be adapted to detect a gaseous analyte (for example, hydrogen). The sensor may, for example, include a plurality of metal particles/nanoparticles decorated upon perforated or holey graphene members (for example, generally planar members or flakes) acting as a conducting channel and interdigitated metal electrodes prepatterned on a silicon chip. A variety of metal particles/nanoparticles (for example platinum (Pt), gold (Au), or palladium (Pd)) can be used as analyte interactive material to, for example, detect gaseous analytes such as hydrogen, hydrogen sulfide, nitric oxide, carbon monoxide etc. In other embodiments, a material which interacts with an analyte may be chemically (for example, covalently or ionically) bonded to the hRGO members.

In a number of embodiments, sensor hereof provide a rapid and effective way to sense biomolecular interactions between immobilized biomolecules and target analyte. Examples of suitable analyte interactive materials include, but are not limited to, antimicrobial peptide, DNA, RNA, antibodies, aptamers etc. Such analyte interactive materials may be covalently or non-covalently bound on hRGO to, for example, detect complimentary DNA, RNA, antigens, proteins, viruses, and bacteria.

Representative studies indicated that sensors hereof may, for example, operate at ambient/room temperature and detect an analyte such as hydrogen gas, bacteria etc. through changes in, for example, electrical conductance. In a number of studies, representative sensors hereof were found to exhibit good response, recovery and stability under ambient conditions. Operating sensors hereof at ambient temperature leads to reduced power consumption compared to sensors which must operate at a temperature other than ambient temperature (for example, sensors which must be heated to an elevated temperature range).

In a number of studies, sensors were fabricated by depositing hRGO onto metal electrodes via electric field assistance to form a conducting channel (for example, dielectrophoretically). A metal (for example, platinum or Pt) was thereafter deposited on the hRGO. A metal may alternatively be deposited on the hRGO members prior to formation of the conducting channel (for example, in a suspension including the hRGO members via, for example, a chemical reduction). In a number of embodiments, metal nanoparticles were deposited. The deposition of metal nanoparticles lead to the selective detection of, for example, hydrogen gas concentration. Sensors hereof can, for example, be used for selective electronic detection of hydrogen gas at parts per million (ppm) levels in ambient conditions. High sensitivity and selectivity for hydrogen gas (for example, in the range of approximately 40 ppm to 40 000 ppm) have, for example, been achieved. Moreover, hydrogen sensors hereof exhibited little or no cross sensitivity with other, interfering gases such as carbon monoxide and methane.

In other representative embodiments of sensors, biological agents (for example, bacteria) can be detected by depositing a material which interacts with the biological agent upon the hRGO materials hereof. For example, in a representative embodiment, antimicrobial peptide (AMP) specific to E. coli was covalently functionalized onto holey graphene FET devices. Exposure of FET devices to E. coli solutions of different concentrations resulted in decreasing conductance hRGO FET device with increasing concentrations of E. coli.

In a number of representative studies of the formation of holey graphene oxide, both graphene oxide and RGO samples were incubated with horseradish peroxidase (HRP) at pH 7.0, room temperature, and low concentrations (~40 μM final concentration) of hydrogen peroxide ($H_2O_2$) that were added daily. The resultant dispersions, which included either graphene oxide or RGO with HRP, were classified as colloids based on the Tyndall scattering effect. In addition, a Raman spectroscopy was used to analyze graphene oxide and RGO on days 0, 4, and 20 of incubation with HRP/$H_2O_2$, and the ratio of the D band, which measured the presence of disorder in $sp^2$-hybridized carbon systems, to G band that evaluated stretching of C—C bonds in graphitic materials were compared. For graphene oxide between days 0 and 4, the D:G ratio increased from 1.1:1.0 to 1.6:1.0, and by day 20, both the D and G bands disappeared. For RGO, the D:G ratio between day 0 and 4 decreased from 1.2:1.0 to 1.1:1.0, and increased to 1.3:1.0 by day 20. There were two plausible explanations for the increase in the D:G ratio from 1.1:1.0 to 1.6:1.0 between days 0 to 4 of graphene oxide incubation. First, because Raman spectroscopy was performed on different flakes, the variance in the D:G ratio may have been the result of different degrees of graphene oxide oxidation due to the modified Hummers' method. Secondly, there may have been an increase in the number of defect sites as a result of HRP catalyzed oxidation of the graphitic lattice. The D and G bands disappeared by day 20 as a result of the complete enzymatic oxidation of the graphitic lattice; therefore, Raman spectroscopy provided evidence that graphene oxide underwent oxidation. For RGO samples, Raman data showed an increase in the D:G ratio after graphene oxide was reduced to RGO using hydrazine, similar to previous literature. The fluctuations observed in the D:G ratio for RGO between days 0, 4, and 20 were attributed to variations in samples since different flakes were examined.

Transmission electron microscopy (TEM) was also used to monitor the progression of HRP catalyzed oxidation of graphene oxide over a 20 day period with daily additions of 40 μM $H_2O_2$ (final concentration, FIG. 1A). Initially at day 0, flat sheets with dimensions ranging from 0.5 to 1.5 μm were observed. After 5 days, graphene oxide sheets began to wrinkle; visible holes were formed in the graphitic lattice of the basal plane by day 8. The size of the holes increased with time; at day 8 the average hole size was 2.1±0.6 nm versus 26.7±12.8 nm at day 10 of the oxidation process. By day 12 as the hole size continued to expand, small flakes of graphene oxide were observed, and the majority of graphene oxide was completely oxidized by day 20 of the experiment. In contrast, no oxidation was observed by TEM for the graphene oxide controls (see TEM photographs of FIG. 1B). From the TEM micrographs obtained over the twenty-day period of the study, it was concluded that graphene oxide underwent significant oxidation, which resulted in the formation of holes on its basal plane (represented schematically in FIG. 1C).

The TEM micrographs of graphene oxide at day 8 and 10 of the oxidation process were studied to obtain information regarding the oxidation mechanism. In particular, two parameters were analyzed: the neck width (D) and the hole diameter (d) (see FIG. 1C). Interestingly, as the diameters of the holes increased on average 12 times (2.1±0.6 nm to 26.7±12.8 nm) from days 8 to 10, the neck width remained roughly unchanged (9.4±7.8 nm versus 8.9±6.9 nm for days 8 and 10, respectively). This indicated that enzymatic oxidation did not produce neck widths (i.e. interconnected nanoribbons) smaller than a certain size. As the enzymatic oxidation reaction proceeded, the necks collapsed, which resulted in an increase in the diameters of the holes on average 12 times from days 8 to 10; the neck width, however, remained roughly unchanged for days 8 and 10.

Figure 1B:
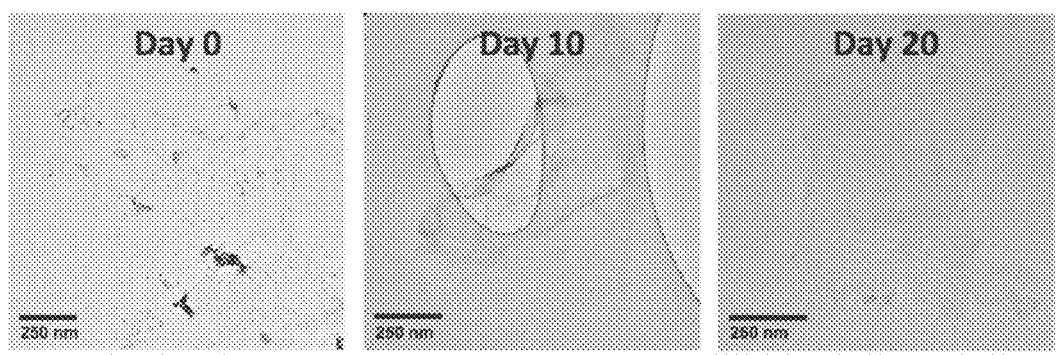
FIG. 1B illustrates TEM micrographs of RGO after 0, 10, and 20 days of incubation with horseradish peroxidase (HRP) and 40 μM hydrogen peroxide ($H_2O_2$).

As determined from TEM, RGO incubated under identical reaction conditions as graphene oxide, failed to undergo oxidation over the same twenty-day period (see FIG. 1B). A colorimetric assay performed with Amplex Red (a reagent commonly employed to measure trace $H_2O_2$ concentrations in biological systems) had a peak for resorufin (the product of HRP catalyzed oxidation of Amplex Red) in the visible region around 570 nm for a sample containing RGO at both day 1 and day 20 of the oxidation process. The assay revealed that at least a portion of HRP retained enzymatic activity in the presence of RGO. This observation was also confirmed by electron paramagnetic resonance spectroscopy. Because there was no visible evidence of enzymatic oxidation for RGO over the twenty-day period of analysis, it appeared that HRP interacted with RGO and graphene oxide differently.

Figure 4A:
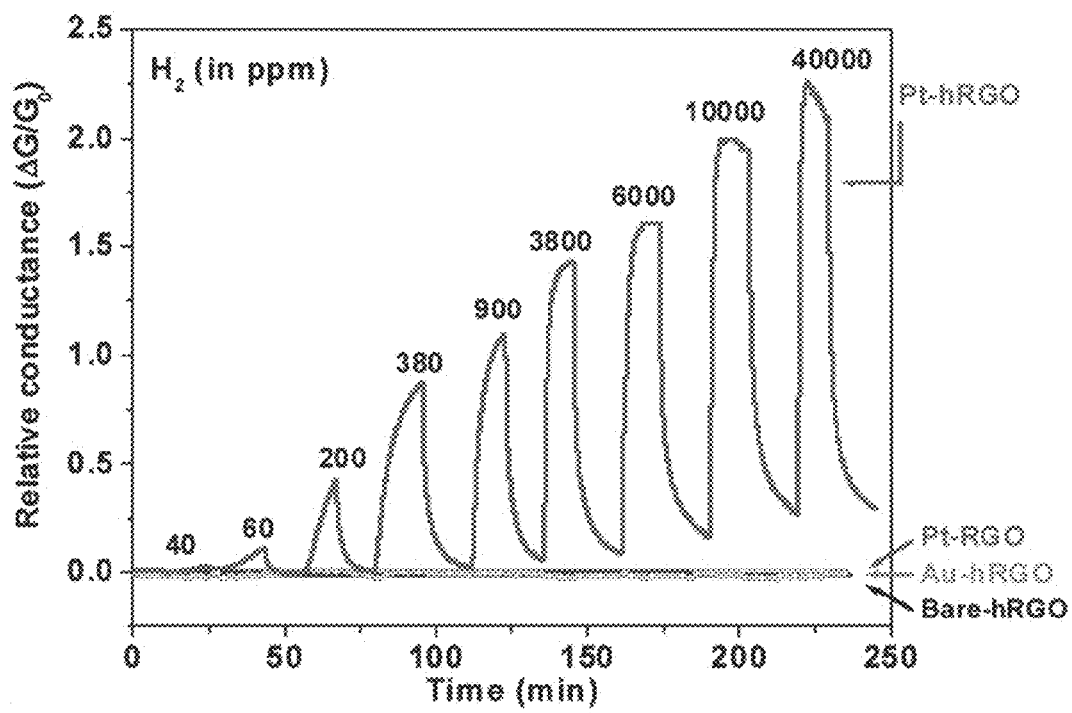
FIG. 4A illustrates the response of Pt-decorated hRGO or Pt-hRGO to hydrogen gas by plotting relative conductance ($\Delta G/G_0$) versus time curves for an $H_2$ concentrations 40 ppm-40 000 ppm (in $N_2$) for Bare-hRGO, Au-hRGO, Pt-hRGO, and Pt-reduced graphene oxide (RGO); wherein, after each $H_2$ exposure, the devices were allowed to recover in synthetic air.
Figure 4B:
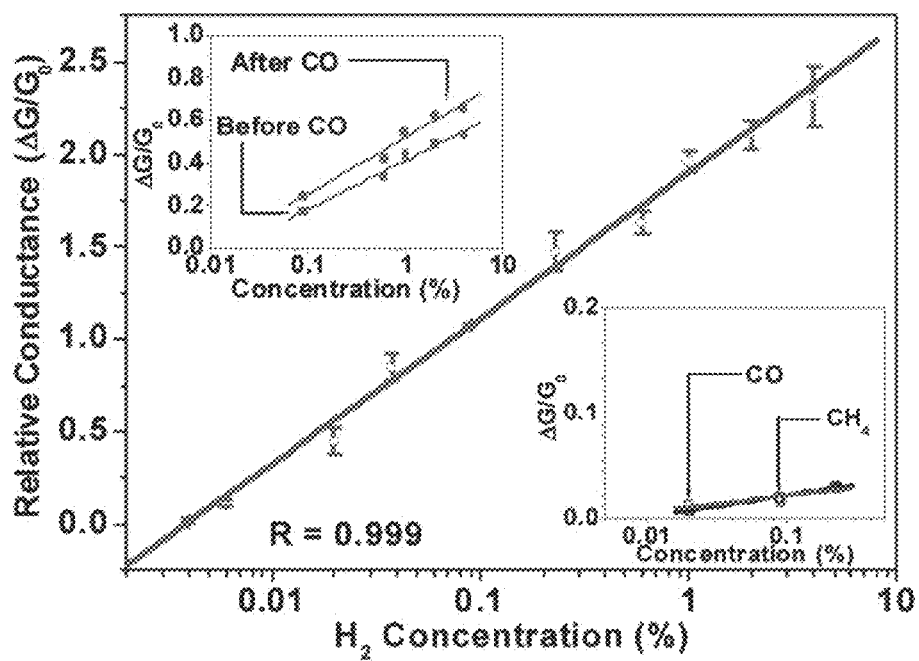
FIG. 4B illustrates a calibration curve of Pt-hRGO for response to $H_2$ gas; wherein the left inset shows the device response to $H_2$ before and after exposure to CO (0.25% in $N_2$), and the right inset shows the response to exposure to CO (0.05-0.25% in $N_2$) and $CH_4$ (0.4-4% in $N_2$).

Graphene oxide, holey graphene oxide, and RGO were further examined by atomic force microscopy. AFM section analysis indicated that graphene oxide had a height of 0.61 nm. Therefore, the exfoliation of graphene oxide by sonication successfully produced a single layer of graphene oxide. Since graphene sheets have a height of 0.34 nm, it was not possible for two sheets to be present (i.e. 0.61 nm<0.68 nm). The presence of covalently attached oxygen functional groups (tertiary alcohols and epoxides) that decorate the basal plane of graphene oxide might be responsible for the added thickness of the graphene oxide flake. In addition, AFM confirmed that HRP binds to graphene oxide. HRP's height was determined by AFM section analysis to be approximately 5 nm. Therefore, the height of 5.37 nm obtained by section analysis (graphene oxide—Day 0) indicated that a single layer enzyme was bound to an individual sheet of graphene oxide. Applying the same reasoning, one could conclude that two layers of enzyme existed on graphene oxide to produce a region where the height was 9.81 nm. The height of the holey graphene oxide sheet was 1.10 nm (a graphene oxide bilayer) with a hole height of 0.01 nm (graphene oxide—Day 10). Finally, AFM section analysis indicated that RGO had a height 1.73 nm, which demonstrated that RGO was formed of an aggregation of flakes. Since the oxygen functional groups on the basal plane were reduced, van der Waals forces dominated between the flakes of RGO resulting in the formation of aggregates. Similar to graphene oxide, AFM confirmed that HRP was bound to RGO during the incubation process; unlike graphene oxide, however, no evidence of oxidation was observed by AFM at day 10 (FIG. 4b, RGO—Day 10). With a total height of 7.59 nm, one layer of enzyme was bound to a RGO aggregate that contained between four to seven sheets.

The ability of HRP to bind with sheets of graphene oxide/RGO was confirmed by sodium dodecyl sulfate polyacrylamide gel electrophoresis (SDS-PAGE), followed by silver staining. Because of size, both graphene oxide and the highly hydrophobic RGO failed to migrate well during gel electrophoresis; therefore, the majority of the material was retained in the stacking region of the gel. A protein band at 44 kDa corresponded to the literature value for HRP. While initially all samples contained 1.1 mg of HRP, the quantity of protein that remained post-incubation with RGO was approximately three times less than the quantity of HRP present in other samples, which indicated that HRP was bound more tightly to RGO than to graphene oxide. Additionally, the results of gel electrophoresis indicated that minimal auto-oxidation took place during both the tested incubation period and for 40 μM levels of $H_2O_2$. In the absence of exogenous oxidizable substrates, monomeric hemoproteins form dimers, trimers, and other oligomers during the activation of their peroxidase. This stems from the recombination of protein-derived (likely, tyrosyl) radicals generated as reaction intermediates and results in the formation of covalent cross-links that are non-dissociable in SDS. Thus if HRP oligomers were formed in the reaction, they should have been detectable in the SDS gel. The lack of HRP oligomers indicated that $H_2O_2$-dependent cross-linking of the enzyme did not take place, and the oxidizing potential of the enzyme was directed towards graphene oxide/RGO oxidation. Without limitation to any mechanism, molecular modeling studies suggested that the presence of epoxy- and hydroxyl groups in the basal plane and the flexibility of the oxidized graphene sheet may be responsible for a preferential enzymatic oxidation of graphene oxide and holey graphene oxide versus RGO by HRP.

Product analysis in the sample headspace utilizing gas chromatography—mass spectrometry (GC-MS) indicated that $CO_2$ was the final product of complete enzymatic catalyzed oxidation. Sample headspace of sealed vials in which HRP was incubated with either graphene oxide or RGO was extracted, and the concentration of $CO_2$ was determined. By day 10, the concentration of $CO_2$ increased by 65% for graphene oxide and 2% for RGO over ambient; whereas the controls for graphene oxide (—HRP, —$H_2O_2$, and —graphene oxide) indicated only a 2-4% increase in relative $CO_2$ levels at day 10. With over thirty times the amount of $CO_2$ produced for graphene oxide oxidation compared to the RGO control, the Raman and TEM results, which indicated that graphene oxide underwent HRP catalyzed oxidation, were substantiated via GC-MS product analysis.

Amplex Red was used to monitor the concentration of the substrate, $H_2O_2$, as a function of time to yield enzyme kinetics. HRP incubated with graphene oxide and $H_2O_2$ demonstrated that 97% of the substrate was consumed within 30 minutes. In all studies discussed above, $H_2O_2$ was added on a daily basis at a concentration of 40 μM to facilitate thorough characterization of the oxidation products. Taking into account the enzymatic kinetic data, additional experiments were conducted wherein $H_2O_2$ was added every 30 minutes. For the resulting data, holes were observed in the basal plane of graphene oxide after 4.5 hours. Because of the quick rate of enzymatic oxidation once holes were formed, may samples of the graphene oxide became "overly oxidized" or overly degraded. Attempts to shorten the total oxidation time by 15 minutes (i.e. for a total oxidation time of 4.25 hours) yielded pristine graphene oxide sheets. A window thus existed, where hole formation occurred. With respect to reproducibly generating holey graphene oxide, the multi-day approach was thus advantageous, and holey graphene oxide has been produced numerous times utilizing this technique for the studies hereof. In a number of other studies, a higher concentration of $H_2O_2$ was used in a multi-day, daily addition scheme. In such studies, 4 μL of 0.1 M $H_2O_2$ were added to a graphene oxide dispersion on a daily basis for a total of four days (i.e. a total of four additions) to produce holey graphene oxide on a reproducible basis. Although a multi-day scheme with daily addition of $H_2O_2$ proved advantageous in a number of studies hereof, there was no attempt to optimize results.

Creating holes in graphene enables fine-tuning the electronic properties thereof. As a result of its zero bandgap, graphene is a semimetal. This property limits graphene's utility in some electronic applications such as room temperature field-effect transistors (FETs), which require semiconducting materials. To overcome this limitation, theoretical work has predicted that quantum confinement and edge effects would produce semiconducting properties at room temperature in graphene sheets that have widths less than 10 nm. Indeed, an active area of graphene research involves the fabrication of these quasi-one-dimensional structures referred to as graphene nanoribbons (GNRs). Block copolymer lithography, laser induced photochemical reactions, Joule heating, oxidative etching at temperatures greater than 400° C., and two-dimensional polymer synthesis have been employed to create nanometer sized holes on individual sheets of graphene. As a sheet of perforated graphene can be conceptualized as interconnected nanoribbons, the creation of holes in the basal plane of graphene opens its bandgap to yield a semiconducting nanomaterial.

Figure 2A:
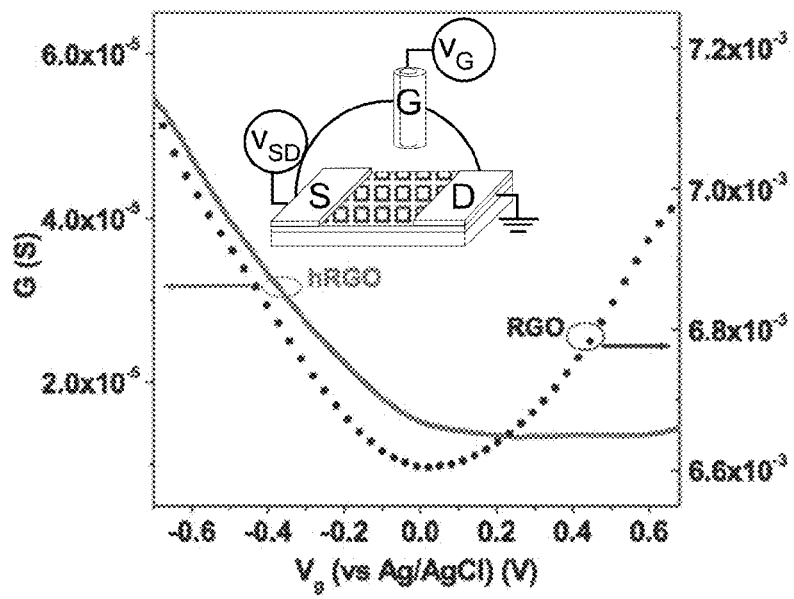
FIG. 2A illustrates conductivity versus potential (liquid gate) plot for reduced graphene oxide (RGO, black circles) and holey reduced graphene oxide (hRGO, solid line); wherein the measurements were recorded in 10 mM KCl/10 mM PBS (pH 7) at a constant drain-source voltage of 10 mV, and wherein the inset represents a schematic of the experimental setup.
Figure 2B:
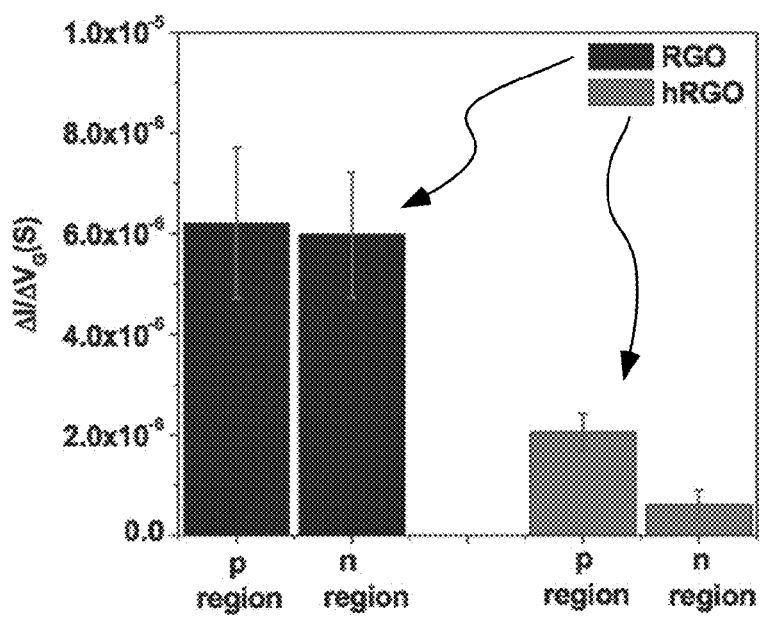
FIG. 2B illustrates a comparison of transconductance ($\Delta I/\Delta V_G$) values of n and p region of 12 different RGO and hRGO FET devices (6 devices each).

To test if the side-product of enzymatic oxidation has unique electronic properties, holey graphene oxide that was formed after 8 days of oxidation (as described above) was reduced with hydrazine to yield hRGO flakes. That material demonstrated electrical conductivity. Both liquid-gated and back-gated FET measurements were implemented on RGO and hRGO (FIG. 2A). For both of the measurement techniques, similar electronic transport characteristics were observed with the liquid gate measurement demonstrating more effective tuning of charge carriers. RGO exhibited a V-shaped transfer characteristic (FIG. 2A) similar to a single layer of graphene, which can be attributed to the zero band gap of graphene. In comparison, hRGO exhibited a decrease in conductance with a p-type behavior and a positive shift in the Dirac points (FIG. 2A). The comparison of transconductance ($\Delta I/\Delta V_g$) values for the n and p regions (FIG. 2B) obtained from 12 different RGO and hRGO FET devices (6 devices each) confirmed the repeatability of the enhanced p-type semiconducting behavior of hRGO compared to RGO.

The observed p-type behavior for hRGO samples can be attributed to the presence of holes in the basal plane of the graphene nanomaterial. Without limitation to any mechanism, the formation of holes in the basal plane may have resulted in the opening of the band gap as a consequence of lateral quantum confinement and the presence of additional oxygen-containing functional moieties (i.e. carboxylic acids, lactols, quinines, hydroquinones, etc.) around the holes that were introduced during the enzymatic oxidation process.

In a number of studies of sensor devices formed using RGO and hRGO FET devices were fabricated by patterning interdigitated microelectrodes (source-drain spacing of 10 μm) on top of 200 nm oxide layer on Si substrates using photolithography and e-beam evaporation of 30 nm Ti and 100 nm of Au. RGO and hRGO flakes as described above were used as conducting channels in these sensor devices. Dielectrophoresis (DEP) technique was used for selective deposition of RGO and hRGO flakes from DI water/NH$_4$OH suspension onto each interdigitated microelectrode pattern. The dielectrophoresis parameters (namely, a.c frequency (300 kHz), bias voltage (8 V$_{pp}$), and bias duration (120 s)) were used to fabricate hRGO and RGO devices. Each Si chip, including multiple devices, was then placed onto a standard ceramic dual in-line package (CERDIP) and wire-bonded. To study the transfer characteristics, FET devices were tested using the Si substrate as a backgate and measurements were made using two Keithley 2400 sourcemeters available from Keithley Instruments, Inc. of Cleveland, Ohio. All the devices were operated at a constant source-drain voltage of 50 mV and had electrical conductance in the range of 1 µS-100 µS and 100 µS-10 mS for hRGO and RGO devices, respectively.

Figure 3A:
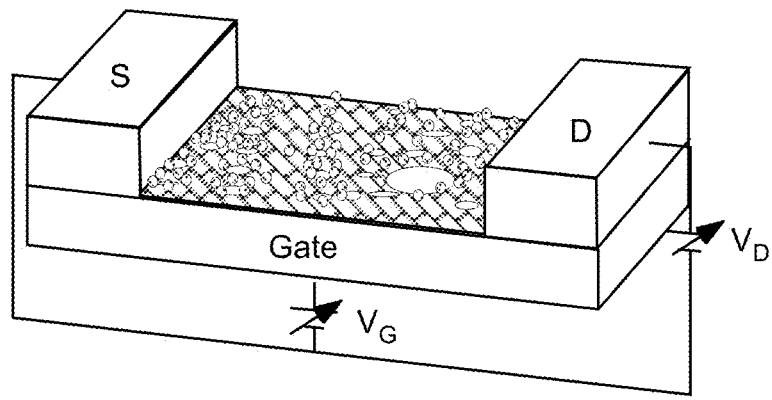
FIG. 3A illustrates an embodiment of an hRGO device wherein the hRGO is decorated with a material such as metal nanoparticles for interacting with an analyte.
Figure 3B:
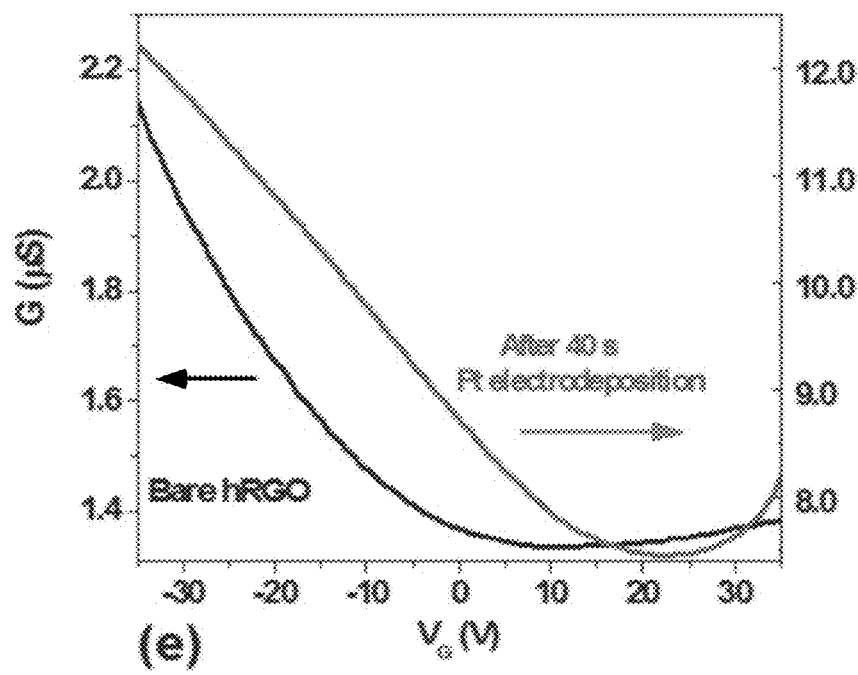
FIG. 3B illustrates room-temperature field-effect transistor (FET) characteristics (source-drain conductance, G, versus back gate voltage, $V_G$) of hRGO before and after 40 s Pt electrodeposition, wherein a constant source-drain voltage ($V_{ds}$) of 50 mV was applied.

The flakes were decorated with platinum or gold nanoparticles by pulsed potentiostatic electrodeposition from aqueous solutions containing Pt$^{4+}$ or Au$^{3+}$ metallic ions using an electrochemical analyzer (available from CH Instruments of Austin, Tex.) by connecting the source and drain pins of a single device and using it as the working electrode in an electrochemical cell. Specifically, a fluid chamber was placed over the chip to contain a small volume (~100 µL) of 1 mM H$_2$PtCl$_6$ (for Pt) or HAuCl$_4$ (for Au) (from Sigma Aldrich of St. Louis, Mo.) in a supporting electrolyte of 0.1 M HCl; Ag/AgCl (3 M KCl) reference and Pt wire counter electrodes were placed in the chamber to create a miniaturized electrochemical cell. The working electrode was immersed in the platinum plating solution at a potential of +0.8 V vs. Ag/AgCl followed by stepping the potential of the working electrode surface from this initial value to a deposition potential of −0.7 V. Following the application of the deposition pulse, the electrode potential was returned to +0.8 V vs. Ag/AgCl, and the working electrode was removed from the plating solution. The deposition potential of −0.7 V for Pt (−0.35 V for Au) was held for a time between 10 and 60 s to deposit metal nanoparticles of various sizes on the hRGO and RGO devices. FIG. 3A illustrates a schematic of the studied hRGO FET device decorated with metal nanoparticles. The transfer characteristics of such devices before and after electrodeposition are illustrated in FIG. 3B. The nanoparticle formation was characterized by scanning electron microscopy (SEM), high resolution transmission electron microscopy (HRTEM), and energy dispersive X-ray spectroscopy (EDX).

FIG. 3B shows the transfer characteristics of a bare and Pt NP decorated hRGO FET devices. Compared to RGO FET devices which were ambipolar, the bare hRGO devices exhibited p-type behavior I$_{on}$/I$_{off}$ of 1.6 at room temperature with Dirac point near V$_g$=0 V. This p-type behavior of hRGO can be attributed mainly to the presence of holes (average diameter=16.7±7.2 nm) in the basal plane, which resulted in a highly interconnected network of graphene nanoribbons that were 9.2±5.1 nm wide. A gradual increase in conductance and a positive shift in Dirac points were observed after Pt NP electrodeposition for 40 sec.

The electronic response of metal NP decorated RGO and hRGO devices to Hz gas exposure at room temperature was studied. Measurements were carried out on a test-board using Zephyr software. Employing a Kiethley 2602 dual-source meter and Keithely 708A switching mainframe, all devices (four) on a single chip were monitored at a given time. Device switching was performed at 500 milliseconds, displaying near-real time responses for each device. FIG. 4A shows the relative conductance change (ΔG/G$_0$) versus time plots for bare hRGO, Pt-hRGO, Pt-RGO and Au-hRGO. The Hz concentration was varied from 40 parts per million (ppm) to 40,000 ppm (in N$_2$), and the recovery step was performed by purging synthetic air into the test chamber. Among all tested devices, only Pt-hRGO exhibited enhanced response towards Hz gas with detection limit of 60 ppm (S/N >3). Pt nanoparticle decorated RGO has been shown to detect Hz at either high concentrations (40,000 ppm) or higher temperatures, whereas Pd decorated graphene nanoribbons networks exhibited a detection limit of 40 ppm for Hz. In the present studies, Pt-RGO devices did not exhibit any significant response to Hz at room temperature in the tested range (40-40,000 ppm). Since both Pt-RGO and Pt-hRGO had similar coverage of Pt nanoparticles on their basal planes. Without limitation to any particular mechanism, the high Hz sensitivity of Pt-hRGO was attributed to the Pt nanoparticles decorating the edges.

FIG. 4B illustrates calibration curve for Hz gas measured using five different Pt-hRGO devices. The influence of CO, CH$_4$, and relative humidity on Hz sensing with Pt-hRGO devices was also studied. The devices showed no significant response towards CO (0.25%) and CH$_4$ (4%) (right inset FIG. 4B) when measured either in N$_2$ or air as background. Additionally, no evidence of Pt poisoning as a result of CO exposure was observed for these devices (left inset, FIG. 4B). Finally, the response of Pt-hRGO devices to H$_2$ was not significantly affected either by relative humidity fluctuations within the tested range of 11% to 78% or as a result of an O2 environment when tested in air as background.

Figure 4C:
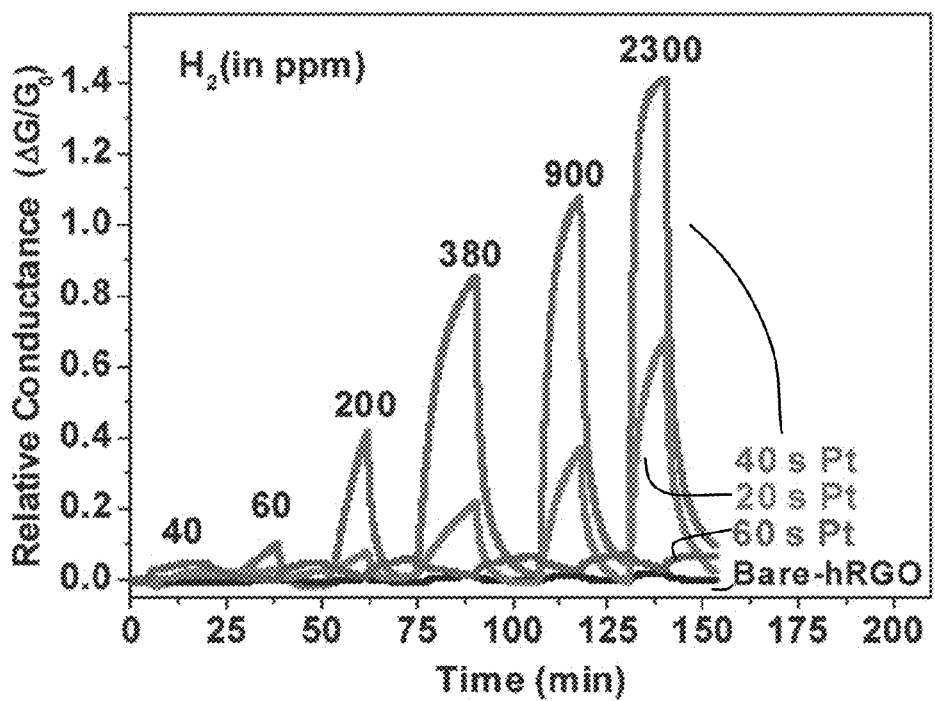
FIG. 4C illustrates relative conductance ($\Delta G/G_0$) versus time curves, demonstrating $H_2$ response of Pt-hRGO devices with different Pt nanoparticle electrodeposition durations (that is, 0, 20, 40, and 60 seconds).
Figure 4D:
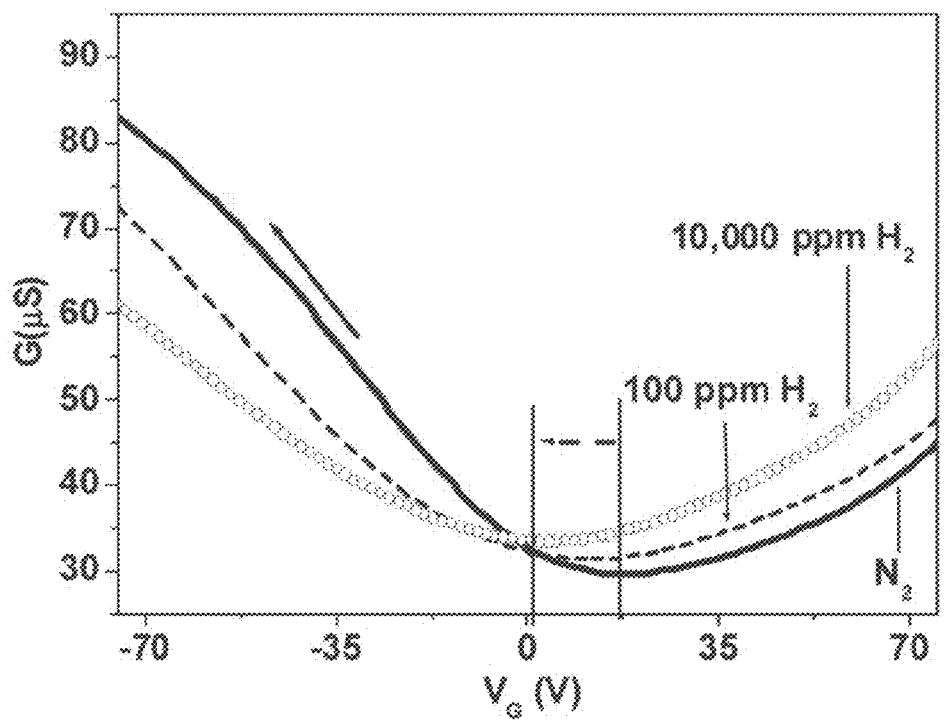
FIG. 4D illustrates conductance (G) versus gate voltage ($V_G$) curves of Pt-hRGO FET devices at 0, 100, and 10 000 ppm of $H_2$ (in $N_2$) exposures with a constant source-drain bias ($V_{ds}$) of 0.5 V.

The sensitivity of the hRGO devices was dependent on the Pt catalyst concentration (see FIG. 4C). In the present studies, electrodeposition for 40 s provided the highest sensitivity (FIG. 4C). Longer deposition times resulted in the formation of a continuous Pt film on hRGO, which was confirmed by SEM. In addition to conductance versus time measurements, backgated FET characteristics for hRGO devices were collected before and after 10 min of H$_2$ (100 ppm and 10,000 ppm) exposure in N$_2$ (FIG. 4D). For the measured gate voltage range (−75 V to +75 V), the Pt-hRGO devices exhibited an ambipolar characteristic. The introduction of H$_2$ gas resulted in a downward tilt and a negative shift (e.g., ~17 V shift for 10,000 ppm H$_2$) of the curve. Without limitation to any mechanism, this shift may be attributed to electron transfer to the graphene FET channel upon H$_2$ exposure. With an increase in the concentration of H$_2$ gas, a gradual increase in conductance was observed for V$_G$ ~0 V (the gate voltage at which the sensor devices were operated). This observation correlated with the observed increase in conductance illustrated in FIG. 4A. Although Pt-hRGO FET devices exhibited some hysteresis, the shift was consistent for both forward and reverse sweeps. Even though the devices hereof were not optimized, the Pt-hRGO devices hereof exhibited sensitivity with a detection limit of 60 ppm.

Figure 5A:
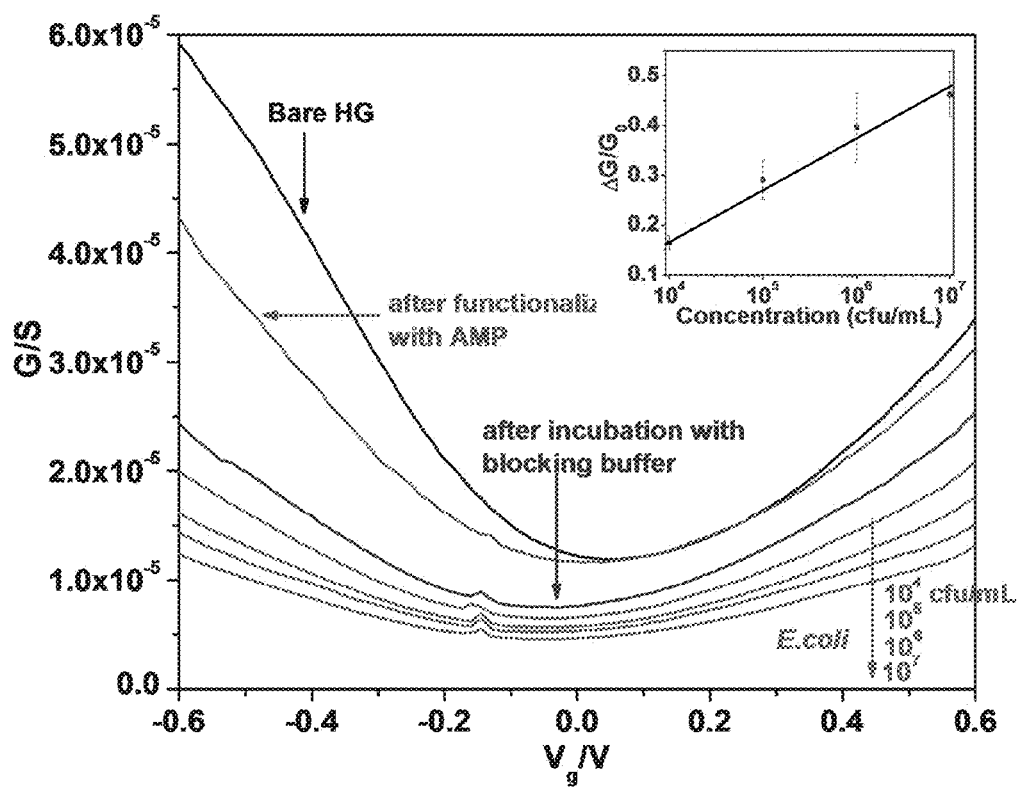
FIG. 5A illustrates conductance (G) versus gate voltage ($V_G$) curves of FET devices in which antimicrobial peptide (AMP) specific to E. coli O157:H7 was covalently functionalized onto holey graphene (HG) FET for E. coli O157:H7 solutions of different concentrations.
Figure 5B:
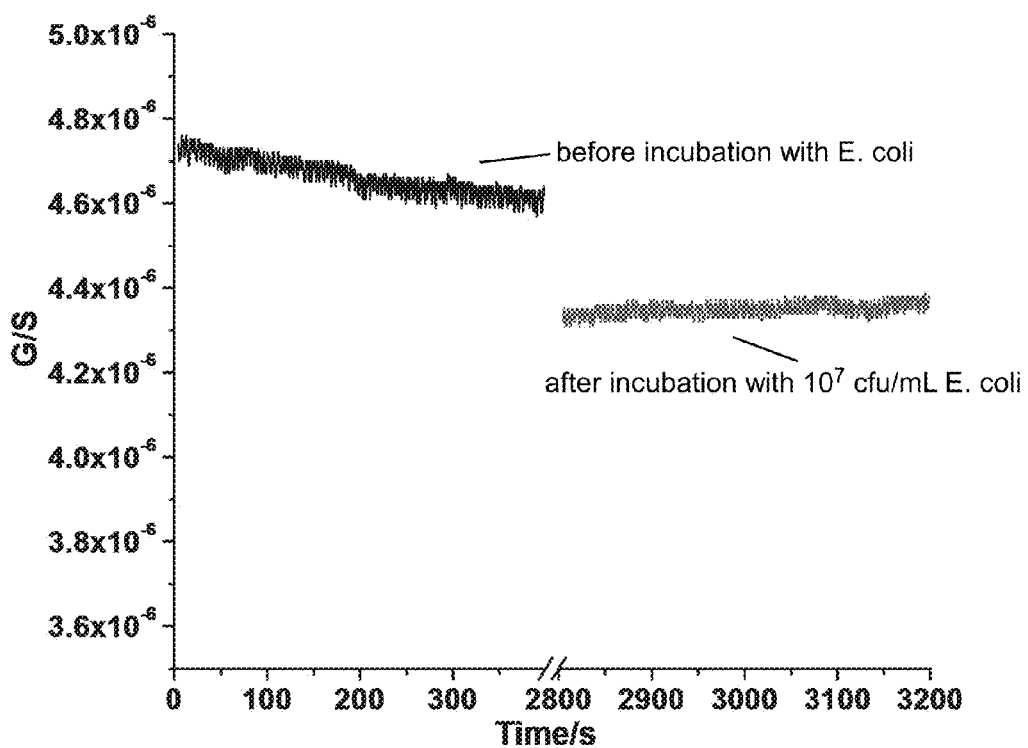
FIG. 5B illustrates conductance (G) as a function of time (s) for the devices of FIG. 5A before incubation with E. coli and after incubation with $10^7$ cfu/mL E. coli.

A broad range of analyte-interactive materials can be placed in operative connection with the hRGO materials hereof to fabricate sensors which are sensitive to a broad range of analytes. In another set of representative studies, antimicrobial peptide (AMP) specific to *E. coli* O157:H7 was covalently fictionalized onto a holey reduced graphene oxide FET device (HG in FIG. 5A). The carboxylic groups on the surfaces of holey reduce graphene oxide were first activated by incubating with EDC/NHS (100 nmol/25 nmol in 50 mM pH 5.5 MES buffer) for 30 mins and then the device was incubated with AMP solution (20 µM in PBS) overnight. After incubation with the blocking buffer to prevent non-specific binding, the device was exposed to *E. coli* O157:H7 solutions of different concentrations. FIG. 5A illustrates conductance (G) versus gate voltage (VG) curves of FET devices in which antimicrobial peptide (AMP) specific to *E. coli* O157:H7 was covalently functionalized onto holey graphene (HG) FET for *E. coli* O157:H7 solutions of different concentrations. Conductance of the HG FET decreased with the increasing concentrations of *E. coli*. FIG. 5B illustrates conductance (G) as a function of time (s) for the devices of FIG. 5A before incubation with *E. coli* and after incubation with $10^7$ cfu/mL *E. coli*.

EXPERIMENTAL METHODS

Materials. Graphite flakes, lyophilized HRP type VI, PBS, hydrazine hydrate (50 wt %), and 30% $H_2O_2$ were purchased from Sigma Aldrich. AMPLEX® Red was purchased from Molecular Probes, Inc. of Eugene, Oreg., Invitrogen, and the SILVERSNAP® stain kit was acquired from Thermo Scientific of Rockford, Ill.

Preparation of Graphene Oxide and RGO. Graphite oxide was prepared utilizing a modified Hummers' method on graphite flakes that underwent a preoxidation step. See Kovtyukhova, N. I.; Ollivier, P. J.; Martin, B. R.; Mallouk, T. E.; Chizhik, S. A.; Buzaneva, E. V.; Gorchinskiy, A. D., Layer-by-Layer Assembly of Ultrathin Composite Films from Micron-Sized Graphite Oxide Sheets and Polycations. *Chem. Mater.* 1999, 11, 771-778. Graphene oxide (~0.125 wt %) was formed from graphite oxide that was diluted 1:4 with double distilled water and exfoliated for 30 minutes by ultrasonication followed by 30 minutes of centrifugation at 3400 r.p.m to remove unexfoliated graphite oxide. Atomic force microscopy (AFM), Fourier transform infrared spectroscopy (FT-IR), ultraviolet-visible spectroscopy (UV-vis), and transmission electron microscopy (TEM) were employed to characterize the exfoliated graphene oxide as described above. Graphene oxide had a sheet height of 0.61 nm, which was determined by section analysis and confirmed that a single layer of graphene oxide was present. Additionally, as evident by the FT-IR spectrum, major peaks appeared around 3400 $cm^{-1}$, 1700 $cm^{-1}$, and 1000 $cm^{-1}$, which were attributed to O—H, C═O, and C═O stretching vibrations, respectively. Moreover, FIG. 1A illustrates a single sheet of graphene oxide as captured by TEM.

Figure 1C:
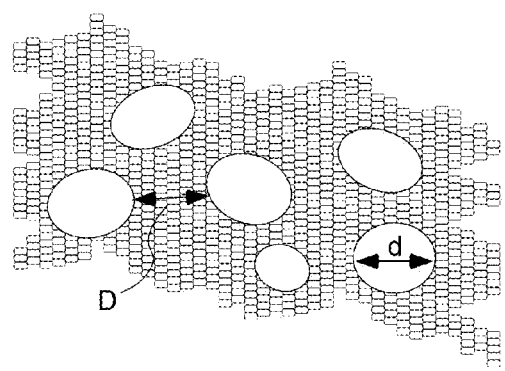
FIG. 1C illustrates an idealized representation of neck width (D) and hole diameter (d) formed in the basal plane of graphene oxide via peroxidase catalyzed oxidation.

Graphene oxide was reduced to form RGO employing hydrazine hydrate, and RGO was dispersed in water with ammonium hydroxide at a pH around 10 following a published procedure. A mixture containing 5.0 mL of 0.125 wt % graphene oxide, 4.8 mL of double distilled water, 200 μL of hydrazine hydrate (50 wt %), and 35 μL of $NH_4OH$ (28 wt %) was stirred for 5 minutes and heated at 95° C. for 1 hour. The suspension containing RGO was subsequently dialyzed against distilled water to remove hydrazine and $NH_4OH$. RGO had a sheet height of 1.73 nm, which was determined by section analysis and confirmed that between three to five layers of RGO was present. The FT-IR spectrum for RGO showed a reduction in the O—H stretch around 3400 $cm^{-1}$, and carbonyl groups appeared around 1700 $cm^{-1}$. FIG. 1C illustrates a TEM micrograph of RGO. The UV-vis spectrum of RGO displayed a shoulder around 327 nm.

Incubation with HRP and $H_2O_2$. Three vials were prepared by adding 2.0 mL of the 0.125 wt % graphene oxide dispersed in double distilled water. Lyophilized HRP type VI was solubilized in 1× phosphate buffered saline (PBS) (11.9 mM phosphates, 137 mM NaCl, and 2.7 mM KCl) at 0.390 mg $mL^{-1}$ and added to two of the vials containing graphene oxide at a volume of 4.0 mL. This created two vials with a total volume of 6.0 mL (active and control I, —$H_2O_2$) and one with a total volume of 2.0 mL (control II, —HRP). Next, 3.5 mL, 4.0 mL, and 7.5 mL of 1×PBS were added to active, control I, and control II, respectively, for a total volume of 9.5 mL, 10.0 mL and 9.5 mL. For final product analysis, all vials were then sealed with a septum and wrapped with parafilm to create an airtight seal. The identical procedure was followed to prepare three vials for RGO. An additional control III vial (—graphene oxide) was created by adding 4.0 mL of HRP and 5.5 mL of 1×PBS. A sample of 0.5 mL of 800 μM $H_2O_2$ was added by needle through the septum to the active, control II, and control III vials; this started the oxidation reaction. Daily additions of 4 μL of 0.1 M $H_2O_2$ were added to the active, control II, and control III vials; this was continued on a daily basis for twenty days.

Modified Preparation of Holey Graphene Oxide—HRP. 2.0 mL of 0.125 wt % graphene oxide dispersed in double distilled water, 4.0 mL of 100 U $mL^{-1}$ (40 U $mL^{-1}$, final concentration) HRP (type VI) solubilized in 0.1 M phosphate buffer (pH=7.0), and 4.0 mL of 0.1 M phosphate buffer (pH=7.0) were mixed without sonication and incubated overnight at 25° C. with shaking. On a daily basis, 4 μL of 0.1 M $H_2O_2$ were added to the graphene oxide dispersion for a total of four days (i.e. a total of four additions). The sample was protected from light and incubated with shaking during the enzymatic oxidation process. On day 5, the sample was heated to ~100° C. to denature HRP. Alternatively, ~0.30 wt % suspension of graphene oxide dispersed in double distilled water, 4.0 μL of 50 U $mL^{-1}$ (~800 μU $μL^{-1}$, final concentration) HRP (type VI) solubilized in 0.1 M phosphate buffer (pH=7.4), 15.0 μL diethylene triamine pentaacetic acid (DTPA), and 208.0 μL of 0.1 M phosphate buffer (pH=7.4) were mixed without sonication. Every 45 minutes, 1 μL of 18.75 mM $H_2O_2$ was added to the graphene oxide dispersion for a total of 8 additions. The sample was incubated at 37° C. without shaking between additions, and after the 8 additions, the suspension was permitted to incubate for 16 hours at 37° C. without shaking and further hydrogen peroxide additions. After 16 hours, the sample was heated to ~100° C. to denature HRP.

Preparation of Holey Graphene Oxide—myeloperoxidase (MPO). In addition to preparation holey graphene oxide via oxidation with HRP and $H_2O_2$, holey graphene oxide was also prepared using MPO and $H_2O_2$. In such studies, ~0.30 wt % suspension of graphene oxide dispersed in double distilled water, 4.0 μL of ~50 U $mL^{-1}$ MPO (~800 μU $μL^{-1}$, final concentration) solubilized in 0.1 M phosphate buffer (pH=7.4), 15.0 μL diethylene triamine pentaacetic acid (DTPA), and 208.0 μL of 0.1 M phosphate buffer (pH=7.4) were mixed without sonication. Every 45 minutes, 1 μL of 18.75 mM $H_2O_2$ was added to the graphene oxide dispersion for a total of 8 additions. The sample was incubated at 37° C. without shaking between additions, and after the 8 additions, the suspension was permitted to incubate for 16 hours at 37° C. without shaking and further hydrogen peroxide additions. After 16 hours, the sample was heated to ~100° C. to denature HRP.

Preparation of Holey Reduced Graphene Oxide (hRGO). A sample of holey graphene oxide subjected to 8 days of oxidation was reduced to form hRGO employing hydrazine hydrate in an aqueous suspension containing ammonium hydroxide at a pH around 10. A mixture containing 5.0 mL of 0.125 wt % holey graphene oxide, 4.8 mL of double distilled water, 200 μL of hydrazine hydrate (50 wt %), and 35 μL of $NH_4OH$ (28 wt %) was stirred for 5 minutes and heated at 95° C. for 1 hour. For electronic applications, the suspension containing hRGO was subsequently dialyzed against distilled water with 0.5% $NH_4OH$ to remove hydrazine. Alternatively, for enzymatic studies, the suspension containing hRGO was dialyzed against distilled water to remove hydrazine and NH$_4$OH. The FT-IR spectrum for RGO depicted a reduction in the O—H stretch around 3400 cm$^{-1}$, and carbonyl groups appeared around 1700 cm$^{-1}$. Moreover, the UV-vis spectrum demonstrated a well-defined peak around 327 nm.

Raman Spectroscopy. Samples were prepared by dropcasting approximately 20 μL of graphene oxide or RGO at days 0, 4, or 20 on a quartz microscope slide and drying. All spectra were collected on a Renishaw inVia Raman microscope using an excitation wavelength of 633 nm. Samples were scanned from 1000-3000 cm$^{-1}$ to visualize the D and G bands. Spectra were collected with a 15 second exposure time and averaged across 5 scans per location; a total of 10 locations were selected per sample.

Transmission Electron Microscopy. Samples in PBS suspension were first centrifuged at 3400 r.p.m. for 30 minutes and decanted of supernatant in order to effectively remove salt contributions from the buffer. The sample was resuspended into approximately 1 mL of double distilled H$_2$O by sonication for one minute. One drop of the suspended sample was placed on a lacey carbon grid (available from Pacific-Grid Tech of San Francisco, Calif.) and allowed to dry in ambient conditions for 2 hours prior to TEM imaging (FEI Morgagni of Hilsboro, Oreg., 80 keV).

Atomic Force Microscopy (AFM). A Multimode scanning probe microscope (available from Bruker Nano, Inc. of Santa Barbara, Calif.) was utilized in tapping mode for height, phase, and sectional analysis. Sample preparation was performed on freshly cleaved mica that was treated with approximately 20 μL of 0.1% (w/w) poly-L-Lysine (aq) through spin-coating at 1,400 r.p.m. Approximately 10 μL of sample (aq) was spin-coated at 1,400 r.p.m. and allowed to dry in ambient for 45 minutes prior to imaging. Using a "supersharp" Si probe (tip radius <5 nm, Applied Nano-Structures, Inc. of Santa Clara, Calif.), tapping mode was performed at a drive frequency of 182.316 Hz, an amplitude set point of 0.2465 V, and a drive amplitude of 216 mV. Images were initially scanned in a 13.1 μm area prior to magnification of relevant areas. Post-imaging processing included section analysis for quantifying cross-sectional heights of samples.

Monitoring HRP Activity with Amplex Red. AMPLEX Red (Molecular Probes, Invitrogen) was employed to test HRP activity. A 10 mM stock solution of AMPLEX Red was prepared by dissolving the reagent in DMSO. To a 250 μL aliquot of sample being tested for enzymatic activity, 234 μL of 1×PBS, 15 μL of 800 μM H$_2$O$_2$ and 1 μL of 10 mM AMPLEX Red were added. After gentle mixing, the UV-Vis spectrum of the sample was taken with 1×PBS used as the background.

UV-vis-NIR Spectroscopy. Aqueous samples (150 μL) were analyzed using a Lambda 900 spectrophotometer (Perkin Elmer of Waltham, Mass.) and 0.20 mL quartz cuvettes (Path length: 1 cm, World Precision Instruments, Inc.). The samples for the AMPLEX Red study were scanned from 300-800 nm. All samples were used without any further treatment or purification.

Electron Paramagnetic Resonance Spectroscopy. To each sample containing HRP (0.35 μM) and etoposide (200 μM), H$_2$O$_2$ (80 μM) was added, and either a full ESR spectra or the time course of the EPR signal was recorded. The duration of the recordings were 10 min for full ESR and 1 min for the time course of the EPR signals.

For the study, a JEOL-RE1× spectrometer at 25° C. outfitted with a gas-permeable Teflon tubing (0.8 mm i.d., 0.013 mm thickness) obtained from Alpha Wire Corp. of Elizabeth, N.J. was utilized. The tube (approximately 8 cm in length) was filled with 70 μL of the mixed sample, folded into quarters, and placed in an opened 3.0 mm i.d. EPR quartz tube. The etoposide phenoxyl radical spectra were recorded under following conditions: 3350 G, center field; 50 G, sweep width; 0.5 G, field modulation; 10 mW, microwave power; 0.03 s, time constant; 2 min, timescane. The time course of etoposide radical EPR signals was obtained by repeated scanning of the field (1.0 G, sweep width; 3350 G, center field; 8 min, timescane) that corresponded to part of the EPR signal.

Polyacrylamide Gel Electrophoresis (PAGE). Four samples were analyzed using gel electrophoresis, which included: a control for horseradish peroxidase (HRP, 1.1 mg) (around 44 kDa) without hydrogen peroxide (H$_2$O$_2$), HRP (1.1 mg) incubated for three hours in the presence of H$_2$O$_2$ (final concentration of 40 μM H$_2$O$_2$ added every 1 hour), and HRP (1.1 mg each) incubated with graphene oxide or reduced graphene oxide (RGO) for three hours in the presence of H$_2$O$_2$ (final concentration of 40 μM H$_2$O$_2$ added every 1 hour). Samples were separated by sodium dodecyl sulfate (SDS) PAGE in Tris-glycine buffer. The running gel contained 10% acrylamide, 0.375 mM tris-HCl buffer (pH 8.8), 0.1% SDS; the stacking gel contained 4% acrylamide, 0.125 mM tris-HCl buffer (pH 6.8), 0.1% SDS. Gels were polymerized by the addition of 0.1% ammonium persulfate and 0.1% TEMED. Running buffer included 250 mM tris, 250 mM glycine, 0.1% SDS. Samples were diluted in the loading buffer containing 0.125 mM tris-HCl (pH 6.8), 1% SDS and boiled for 5 min. Electrophoresis was run at a constant voltage of 130 V. Gels were stained by a SILVER-SNAP kit according to the manufacturer's manual.

Enzymatic Kinetic Studies. AMPLEX Red was employed to measure the concentration of the substrate, H$_2$O$_2$, as a function of time for a constant concentration of HRP (0.390 mg mL$^{-1}$) incubated with graphene oxide (graphene oxide-active). At time t=0, 4 μL of 0.1 M H$_2$O$_2$ was added to the sample for a final concentration of 40 μM. At 5 minute time intervals (for 1 hour), a 249 μL aliquot of sample and 1 μL of 10 mM AMPLEX Red was gently mixed, and the UV-Vis spectrum of the sample was taken with 1×PBS utilized as the background.

Fourier Transform-Infrared Spectroscopy. Graphene oxide, RGO, and hRGO were isolated using TefSep Teflon laminated filters (0.22 μm hole size). Each sample was mixed with KBr and ground into a fine powder using a mortar and pestle. A KBr pellet was formed from the powder using a press, and the transmittance spectrum of the pellet was taken employing an Avatar 360 FT-IR.

Gas Chromatography-Mass Spectrometry (GC-MS). Approximately 2 μL of sample headspace (total headspace volume: 5 mL) was injected into a Shimadzu QP5050A GC-MS unit (Shimadzu Corporation of Kyoto, Japan) equipped with an XTI-F capillary column by sampling through the septum of one of the five vials (graphene oxide-active, graphene oxide-control I, graphene oxide-control II, graphene oxide-control III, and RGO-active) on day 0 and 10 of the oxidation study. A basic temperature program was performed, starting at 100° C. held for one minute, followed by temperature ramping at a rate of 10° C. min$^{-1}$ until a maximum temperature of 325° C. was achieved and held for an additional 10 minutes.

Fabrication and Measurement of Solution- and Back-Gated RGO and hRGO Field-effect Transistors. Field-effect transistors (FETs) were fabricated using standard photolithography process on Si/SiO$_2$ (oxide thickness=200 nm).

The Ti/Au metal contacts (Ti/Au=30/100 nm) were deposited by electron beam evaporation. Individual graphene flakes were dielectrophretically deposited onto interdigitated electrodes at a frequency of 300 kHz and an a.c field of 1.6 MV m$^{-1}$, and devices were annealed in vacuum at 180° C. for 2 hours. The Si chips with graphene flakes were wirebonded and packaged in a 40-pin ceramic dual-inline package. For backgate measurements, the Si substrate served as gate electrode. The electrical performance of the device was measured using two source measuring units (Keithley 2400). The gate potential was swept from −85 V to +85 V with a constant source drain voltage ($V_{ds}$) of 50 mV or from −20 V to +20 V with a constant source drain voltage ($V_{ds}$) of 10 mV.

For solution-gated measurements, a liquid gate potential was applied to Ag/AgCl (3M NaCl) reference electrode. Epoxy resin was used to prevent direct contact between metal electrode and electrolyte, leaving active graphene area exposed to electrolyte solution. A small polymer chamber was placed on the chip and sealed with epoxy to hold a small volume (a few ml) of the electrolyte. Solution gate measurements were performed in 10 mM KCl/10 mM PBS (pH=7), and the gate voltage was swept from −0.75 V to +0.75 V with the $V_{ds}$ kept constant at 10 mV.

Nanoparticles Decoration: RGO and hRGO devices were decorated with Pt or Au nanoparticles via electrochemical deposition using a CH Instruments electrochemical analyzer by connecting the source and drain pins of a single device and using it as the working electrode in an electrochemical cell. For nanoparticles electrodeposition, a fluid chamber was placed over the chip to contain a small volume (~100 µL) of 1 mM $H_2PtCl_6$ (for Pt) or $HAuCl_4$ (for Au) (Sigma Aldrich) in a supporting electrolyte of 0.1 M HCl, and Ag/AgCl (3 M KCl) reference and Pt wire counter electrodes were placed in the chamber to create a miniaturized electrochemical cell. A pulsed potentiostatic method was implemented wherein, the working electrode was immersed in the platinum plating solution at a potential of 0.8 V vs. Ag/AgCl (a potential at which electroless platinum deposition was not observed) followed by stepping the potential of the working electrode surface from this initial value to a deposition potential of −0.7 V. Following the application of the deposition pulse, the electrode potential was returned to 0.8 V vs. Ag/AgCl, and the working electrode was removed from the plating solution. The deposition potential of −0.7 V for Pt (~0.35 V for Au) was held for a time between 10 and 60 s to deposit metal nanoparticles of various sizes on the hRGO and RGO devices.

Material Characterization: The formation of RGO and hRGO structures was characterized using transmission electron microscopy (TEM) imaging (FEI Morgagni, 80 keV or JEOL 2100F, 200 keV), while sensor device and nanoparticle decoration were characterized using scanning electron microscopy (SEM) (Phillips XL30 FEG). TEM samples were prepared by dropcasting 5 µl of either RGO or hRGO suspension in deionized (DI) water onto Au (Ted Pella, Inc. of Redding, Calif.), Formvar (Pacific Grid-Tech) or Lacey carbon TEM grids and were allowed to dry in ambient conditions for 2 h prior to imaging. Later nanoparticles electrodeposition was performed by using the TEM grid as the working electrode in a three electrode electrochemical setup. After electrodeposition, the grid was subsequently rinsed with DI water and dried overnight in ambient conditions. Energy dispersive X-ray spectroscopy (EDX) assembly on the TEM was used for characterizing the composition of metals deposited by electrodeposition.

Fabrication of *E. coli* Sensors. Antimicrobial peptide (AMP) specific to *E. coli* O157:H7 was covalently functionalized onto holey graphene (HG) FET. The carboxylic groups on the surfaces of holey graphene were first activated by incubating with EDC/NHS (100 nmol/25 nmol in 50 mM pH 5.5 MES buffer) for 30 mins and then the device was incubated with AMP solution (20 µM in PBS) overnight. After incubation with the blocking buffer to prevent non-specific binding, the device was exposed to *E. coli* O157:H7 solutions of different concentrations. Conductance of the HG FET decreased with the increasing concentrations of *E. coli*.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A device comprising a component comprising a semiconductive composition formed by oxidation of graphene oxide sheets to form holey graphene oxide having defects comprising a plurality of holes in the basal plane therein and reduction of the holey graphene oxide sheets to provide a network of interconnected graphene nanoribbons between the plurality of holes in the basal plane, the plurality of holes having an average diameter in the range of 1 to 100 nm.

2. The device of claim 1 wherein oxidation of graphene oxide is enzymatic oxidation in the presence of a peroxidase and a substrate for the peroxidase.

3. The device of claim 1 wherein the component comprises a field-effect transistor comprising a layer of the semiconductive composition formed on a substrate between a source and a drain of the field-effect transistor.

4. The device of claim 1 wherein the component is a semiconductive layer of the device comprising the composition.

5. The device of claim 4 further comprising a material interactive with an analyte immobilized upon the reduced graphene oxide.

6. The device of claim 1 wherein the oxidation of graphene oxide sheets comprises enzymatic oxidation of graphene oxide sheets.

7. The device of claim 6 wherein enzymatic oxidation occurs in the presence of a peroxidase and a substrate for the peroxidase.

8. The device of claim 7 wherein the peroxidase is horseradish peroxidase, myeloperoxidase, cytochrome c peroxidase, cytochrome P450, eosinophil peroxidase, glutathione peroxidase, lactoperoxidase, thyroid peroxidase, deiodinase, lignin peroxidase, or manganese peroxidase.

9. The device of claim 8 wherein the substrate includes hydrogen peroxide.

10. The device of claim 6 wherein reduction occurs via reaction with a reducing agent or via heating.

11. A composition comprising graphene oxide sheets comprising a plurality of holes in the basal plane therein formed by oxidation to form a network of interconnected graphene oxide nanoribbons between the plurality of holes in the basal plane, the plurality of holes having an average diameter in the range of 1 to 100 nm.

12. A semiconductive composition comprising a network of interconnected graphene nanoribbons comprising a plurality of holes in the basal plane therein, the plurality of holes having an average diameter in the range of 1 to 100 nm.

13. The composition of claim 11 wherein the oxidation is enzymatic oxidation.

14. The composition of claim 13 wherein enzymatic oxidation occurs in the presence of a peroxidase and a substrate for the peroxidase.

15. The composition of claim 14 wherein the peroxidase is horseradish peroxidase, myeloperoxidase, cytochrome c peroxidase, cytochrome P450, eosinophil peroxidase, glutathione peroxidase, lactoperoxidase, thyroid peroxidase, deiodinase, lignin peroxidase, or manganese peroxidase.

16. The composition of claim 15 wherein the substrate includes hydrogen peroxide.

17. The composition of claim 12 wherein the semiconductive composition is formed by oxidation of graphene oxide sheets to form holey graphene oxide comprising a plurality of holes in the basal plane therein and reduction of the holey graphene oxide sheets to provide the network of interconnected graphene nanoribbons between the plurality of holes in the basal plane.

18. The composition of claim 17 wherein the oxidation is enzymatic oxidation.

19. The composition of claim 18 wherein enzymatic oxidation occurs in the presence of a peroxidase and a substrate for the peroxidase.

20. The composition of claim 19 wherein reduction occurs via reaction with a reducing agent or via heating.

* * * * *